(12) United States Patent
Zou et al.

(10) Patent No.: US 8,564,769 B2
(45) Date of Patent: Oct. 22, 2013

(54) HYPERSPECTRAL IMAGING LIGHT SOURCE SYSTEM

(75) Inventors: Xiaobo Zou, Jiangsu (CN); Jiyong Shi, Jiangsu (CN); Jiewen Zhao, Jiangsu (CN); Xiaoping Yin, Jiangsu (CN); Zhengwei Chen, Jiangsu (CN); Xingyi Huang, Jiangsu (CN); Jianrong Cai, Jiangsu (CN); Quansheng Chen, Jiangsu (CN)

(73) Assignee: Jiangsu University (CN)

( * ) Notice: Subject to any disclaimer, the term of this patent is extended or adjusted under 35 U.S.C. 154(b) by 0 days.

(21) Appl. No.: 13/700,463

(22) PCT Filed: May 24, 2010

(86) PCT No.: PCT/CN2010/000531
§ 371 (c)(1),
(2), (4) Date: Feb. 7, 2013

(87) PCT Pub. No.: WO2011/106913
PCT Pub. Date: Sep. 9, 2011

(65) Prior Publication Data
US 2013/0201350 A1 Aug. 8, 2013

(30) Foreign Application Priority Data
Mar. 4, 2010 (CN) .......................... 2010 1 0117612

(51) Int. Cl.
*G01J 3/00* (2006.01)
(52) U.S. Cl.
USPC ........................................................ 356/300
(58) Field of Classification Search
USPC ....................................... 356/300; 348/207.1
See application file for complete search history.

(56) References Cited

U.S. PATENT DOCUMENTS 7,787,111 B2 * 8/2010 Kim et al. ........................ 356/73
2009/0295910 A1 12/2009 Mir et al.

FOREIGN PATENT DOCUMENTS

| CN | 2874482 Y | 2/2007 |
| CN | 200520099328 | 2/2007 |
| CN | 1995987 A | 7/2007 |
| CN | 200610097857.5 | 7/2007 |
| CN | 101403741 A | 4/2009 |

OTHER PUBLICATIONS

International Search Report; PCT/CN2010/000531; Int'l File Date: May 24, 2010; Jiangsu University et al.; 5 pgs.

(Continued)

*Primary Examiner* — Tarifur Chowdhury
*Assistant Examiner* — Abdullahi Nur
(74) *Attorney, Agent, or Firm* — Schmeiser, Olsen & Watts LLP

(57) ABSTRACT

A hyperspectral imaging light source system includes a light box (1). The light box (1) is a sealed cuboid. In the chamber of the box body a line-scanning camera (2), a beam splitting system (3), an electric control translation platform carrier (5) and the object to be detected (4) on the electric control translation platform carrier, an electric control translation platform screw (6), a linear light source box (7) and a photosensitive diode (8) are respectively provided. A linear light source controller (9), a step motor (10) and a computer (11) are provided outside the box body. The photosensitive diode (8) senses linear light source intensity variation and inputs a feedback signal to the linear light source controller (9). A halogen lamp (13) is installed in the linear light source box (7), and is connected with the linear light source controller (9).

2 Claims, 3 Drawing Sheets

(56) References Cited

OTHER PUBLICATIONS

Written Opinion; PCT/CN2010/000531; Int'l File Date: May 24, 2010; Jiangsu University et al.; 4 pgs.

International Preliminary Report on Patentability; PCT/CN2010/000531; Int'l File Date: May 24, 2010; Jiangsu University et al.; 5 pgs.

* cited by examiner

HYPERSPECTRAL IMAGING LIGHT SOURCE SYSTEM

FIELD OF TECHNOLOGY

The following relates to a hyperspectral imaging technology, in particular, the following relates to a light source system used for hyperspectral imaging which can regulate the light intensity intelligently.

BACKGROUND

Hyperspectral imaging refers to the imaging of a scene over a large number of discrete, contiguous spectral bands such that a complete reflectance spectrum can be obtained for the region being imaged. The basic process of hyperspectral imaging is as follows. Firstly, the light source system gives out light of a certain waveband to irradiate on the surface of an object. Secondly, the light reflects, scatters, and transmits on the surface of the object and inside the object. Thirdly, one part of reflectance light enters the hyperspectral imaging camera beam splitting system and is caught by a sensor inside the camera. At last, hyperspectral images are output after being processed by signals such as photovoltaic conversion. In the hyperspectral imaging process, the light source system plays a very important role. It provides energy input for the whole imaging system. The arrangement of light source system determines the reflection path of the light on the surface of the object. With a steady light source system and a rational light arrangement, it could guarantee the hyperspectral imaging system obtain images with high quality and high stability.

At present, halogen lamps are used as light sources for hyperspectral imaging systems, and diffuse reflection is the main method to obtain the images. For example, in a patent application "A Device For Detecting Agricultural And Animal Products and Method thereof With Hyperspectral imaging Technology" with application number of 200610097857.5, halogen lamps and UV lamps are used as the light sources to obtain the reflected spectral images of the agricultural and animal products. In a patent application "A device For Detecting Fruits and method thereof With Hyperspectral imaging Technology" with application number of 200520099328.x, halogen lamps and laser lights are used as the light sources of the high spectrum image system, the light converges on the surface of the fruits after being transmitted by two optical fibers, and a converging lens is placed in front of the camera lens. Although above-mentioned two disclosed devices can meet the basic requirements for obtaining hyperspectral images, the disadvantages thereof comprise: 1. The light source system are not optimized, for example the luminous efficiency and light intensity will change with the increase of the service life of the halogen lamp, and the energy loss when the light transmits in the optical fibers and so on. 2. The method of the light source to irradiate the object is singular, the method that the light irradiates on the object directly by means of forming a certain angle with the carrier plane can hardly ensure uniform light.

SUMMARY

The purpose of the invention is to overcome disadvantages in the prior art, provide a diffuse line light source system for the hyperspectral imaging which can be optimized and can regulate the light intensity intelligently.

The technical proposal adopted by the invention comprises: the light box is a sealed cuboid, and in the chamber of the box body a line-scanning camera, a beam splitting system, electric control translation platform carrier and the object to be detected on the electric control translation platform carrier, an electric control translation platform screw, a linear light source box and a photosensitive diode; a linear light source controller, a stepper motor and a computer are provided outside the box body; said electric control translation platform carrier is installed in the lower part of the light box and connected to the electric control translation platform lead screw, the electric control translation platform lead screw is connected to the step motor, the linear light source box is installed side above the object to be detected, the photosensitive diode is installed near to the linear light box and is connected with the linear light source controller, the photosensitive diode senses the intensity variation of the linear light source and inputs feedback signals to the linear source controller; the halogen lamp is provided in the line illuminating cylindrical source box, the halogen lamp is connected with the linear light source controller; the line-scanning camera is installed in the upper part of the light box and right above the object to be detected, the line-scanning camera is connected with the beam splitting system and the computer.

Advantages of the invention comprise:
1. Compared with the optical fiber system, this invention can avoid energy loss in detecting, and reduce the system cost, because halogen lamp installed in the illuminating cylindrical box of this invention is directly illuminating the detecting object without optical fiber transmission.
2. The illuminating cylindrical box produces a line of diffuse light source to illuminating the target. It can remove uneven light and enhance the uniform of the light source.
3. The linear light source controller converted 60-Hz AC voltage to a high frequency. At this high frequency, tungsten-halogen lamps do not respond quickly. This simulated a constant DC voltage power supply. Therefore, the stability of the light source is enhanced.
4. Over the lifespan, tungsten-halogen lamps lose their efficiency and produce less light output. A photodiode was placed near a tungsten-halogen lamp to provide feedback to the controller. Based on this feedback, the current input to the tungsten-halogen lamps was increased over the life of the lamp to provide a constant intensity output. Therefore the baseline drift phenomenon in the signal collecting process is restrained, the use efficiency of the light source is enhanced and hyperspectral images with high quality and high stability can be collected.

BRIEF DESCRIPTION OF DRAWINGS

FIG. 2 is an enlarged structure diagram of the linear light source box 7 in FIG. 1; wherein, FIG. 2(a) is an outline drawing of the linear light source box 7, FIG. 2(b) is an arrangement diagram of halogen lamp 13 inside the linear light source box 7.

In the figures: 1. Light box; 2. Line-scanning camera; 3. beam splitting system; 4. Object to be detected; 5. electric control translation platform carrier; 6. Electric control translation platform lead screw; 7. linear light source box; 8. Photosensitive diode; 9. Linear light source controller; 10. stepper motor; 11. Computer; 12. line slot; 13. Halogen lamp.

DETAILED DESCRIPTION

Figure 1:
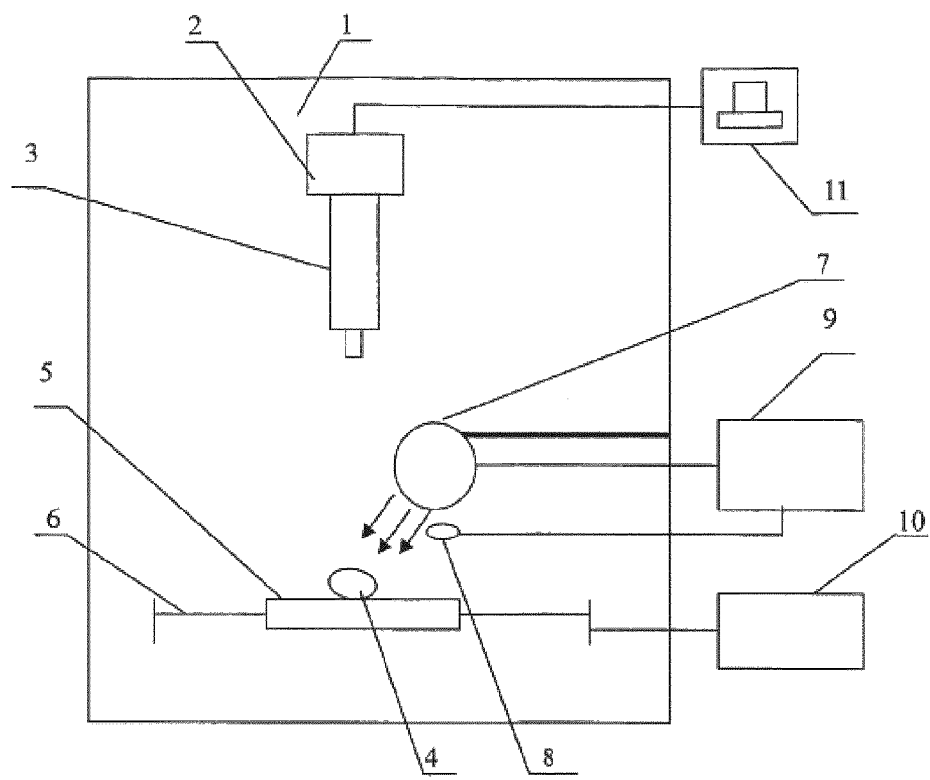
FIG. 1 is a connection diagram of the hyperspectral imaging light source system.

The schematic diagram of the hyperspectral imaging system described in the invention is as shown in FIG. 1, the light box 1 is a sealed cuboid made of stainless steel so as to form an environment-controllable sealed space to prevent influences of the outside light to the hyperspectral imaging and meanwhile to provide a supportive point for mounting other components in the hyperspectral imaging system. The line-scanning camera 2, beam splitting system 3, object to be detected 4, electric control translation platform carrier 5, electric control translation platform lead screw 6, linear light source box 7 and photosensitive dioxide 8 are respectively provided in the chamber of the light box 1. Wherein, electric control translation platform carrier 5 is located in the lower part of the light box 1 and is connected to the electric control translation platform lead screw 6, the electric control translation platform lead screw 6 is connected to the stepper motor 10, the moving speed and direction of the electric control translation platform carrier 6 are controlled by the stepper motor 10. The object to be detected 4 is placed on the electric control translation platform carrier 5, the linear light source box 7 is provided side above the object to be detected 4, the photosensitive dioxide 8 is provided near the linear light source box 7 and is connected to the linear light source controller 9, halogen lamps 13 are provided in the linear light source box 7 and connected to the linear light source controller 9. The line-scanning camera 2 is provided in the upper part of the light box 1 and right above the object to be detected 4, the front part of the line-scanning camera 2 is connected to the beam splitting system 3, the linear scanning camera 2 is connected with the computer.

Figure 2:
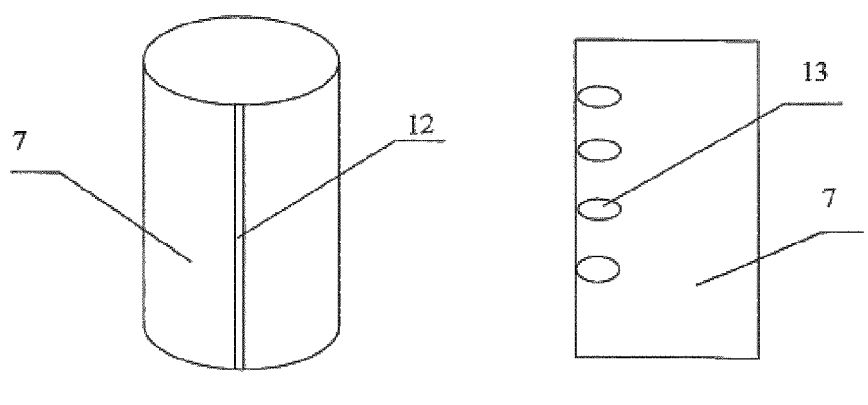
Figure 3A:
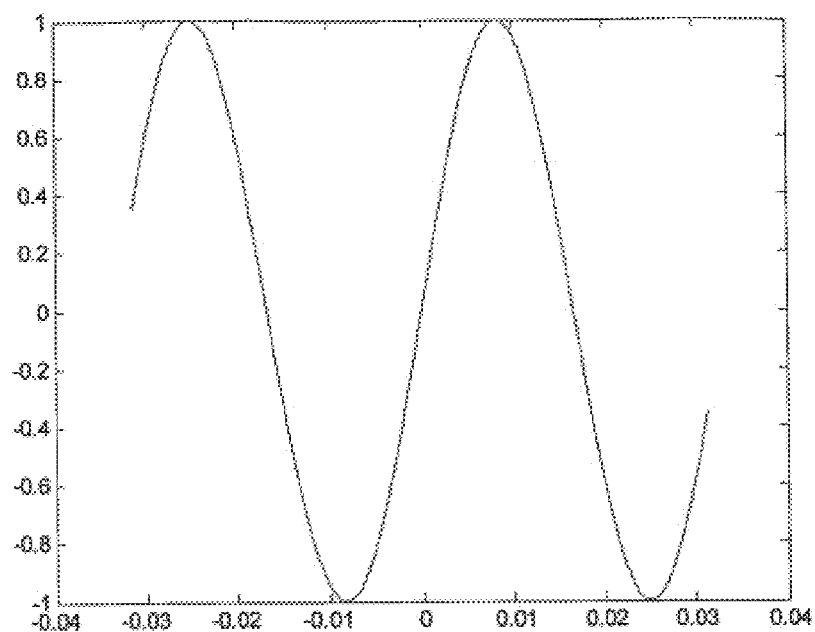
FIG. 3 is an alternating current oscillogram under different frequencies in FIG. 1.
Figure 3B:
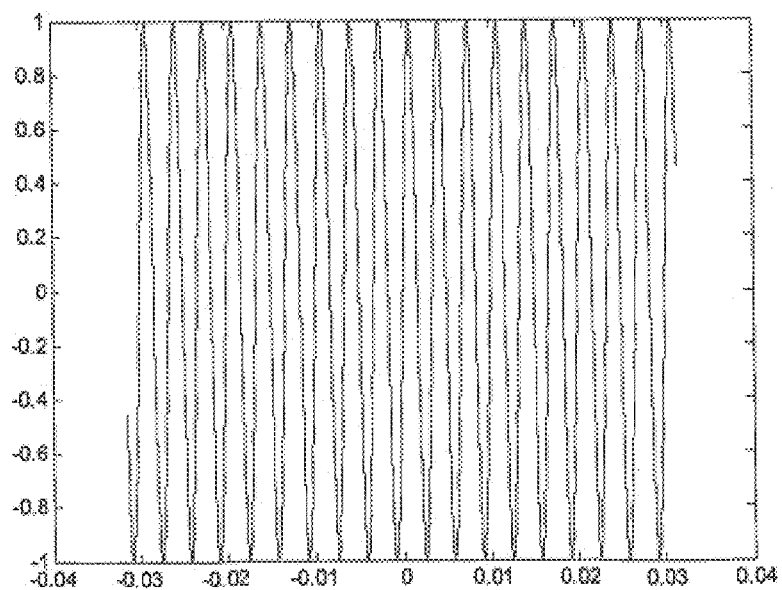
Figure 3C:
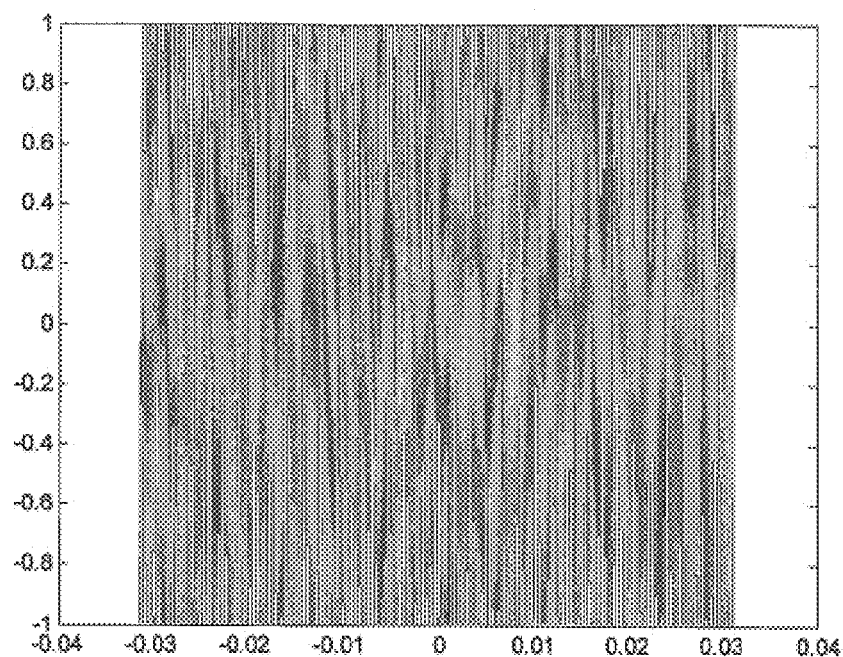
Figure 3D:
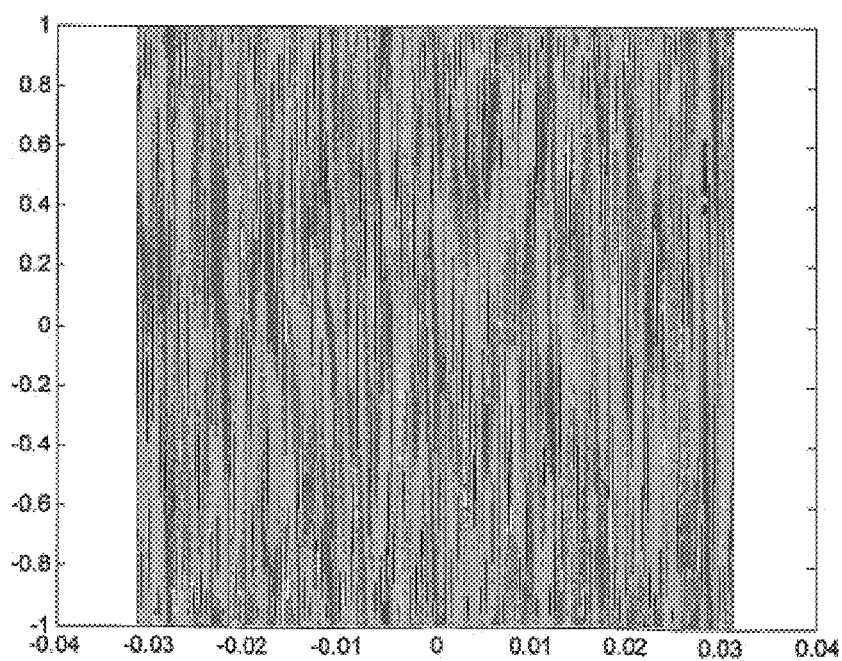

The specific structure of the linear light source box 7 is as shown in FIG. 2, in FIG. 2(a), the linear light source box 7 is a hollow cylinder structure with diameter of 10~25 cm and height of 10~40 cm, the standard of the wall thickness thereof is opaque. The axial wall of the hollow cylinder is provided with a line slot 12, the inner wall of the hollow cylinder is provided with roughness and is sprayed with white paint in order to produce a diffuse light source. As shown in FIG. 2(b), 4~6 halogen lamps 13 are mounted inside the hollow cylinder, the halogen lamps are arranged inside the hollow cylinder in a way of vertical column; after the halogen lamps 13 are powered on, the light has diffuse reflections on the inner wall of the linear light source box 7 so as to form the linear light source needed in the hyperspectral imaging, the diffuse light process can mix the light uniformly so as to ensure that the light casted from the line slot 12 is uniform.

The linear light source controller converted 60-Hz AC voltage to a high frequency. At this high frequency, tungsten-halogen lamps do not respond quickly. This simulated a constant DC voltage power supply.

The role of the linear light source controller 9 is to convert 60-Hz AC voltage to a high frequency. (For example 60 kHz). At this high frequency, tungsten-halogen lamps do not respond quickly. This simulated a constant DC voltage power supply. Therefore, the signal fluctuation caused by blinking of the halogen lamps 13 can be reduced. The photosensitive dioxide 8 can sense the light intensity variation of the linear light source and input a feedback signal to the linear light source controller 9, the linear light source controller 9 senses the light intensity variation in accordance with the feedback signal provided by the photosensitive dioxide 8 and regulates the input current of the linear light source to stabilize the light source intensity and ensure that the linear light source intensity is in the same level, thus the light intensity fluctuation caused by increase of the service life of the light source and change of the external circuit is removed.

The detail process of hyperspectral imaging is as follows: the linear light source box 7 illuminating the object 4 to be detected. The reflected light from the object 4 enters the beam splitting system 3 and then is split into monochromatic light. The split monochromatic light is caught by the line-scanning camera 2. Therefore, a spectral image of the line on the object 4 is obtained. To obtain a three-dimensional (3D) hyperspectral data cube, the object 4 has to be scanned or moved along a second spatial dimension. An electric control translation platform carrier 5 was used to move the object 4 using a stepper motor 10 and an electric control translation platform lead screw 6. The stepper motor was controlled by the computer 11 via a serial port. A scanning rate of line-scanning camera was selected to achieve a cube hyperspectral image which saved in the computer 11.

FIG. 3 is an alternating current oscillogram under different frequencies, the value range of the vertical axis in the figure is [−1, 1], the value range of the horizontal axis is [−$\pi$/100, $\pi$/100], the spacing on the horizontal axis is $\pi$/100000. The frequency corresponding to FIG. 3(a) is 60 Hz, the frequency corresponding to FIG. 3(b) is 600 Hz, the frequency corresponding to FIG. 3(c) is 6000 Hz, and the frequency corresponding to FIG. 3(d) is 60000 Hz. The following conclusion can be drawn from FIG. 3: The wave pattern in a unit length (on the horizontal axis) is denser and denser with the increase of the alternating current frequency, namely the sent out linear light is more stable.

The invention claimed is:

1. A hyperspectral imaging light source system, comprising:
    a light box, a linear light source box and a halogen lamp;
    wherein, the light box is a sealed cuboid, and in a chamber of the light box, a line-scanning camera, a beam splitting system, an electric control translation platform carrier and an object to be detected on the electric control translation platform carrier, an electric control platform screw, a linear light source box and a photosensitive diode are respectively provided;
    wherein a linear light source controller, a stepper motor and a computer are provided outside the light box body;
    wherein the electric control translation platform carrier is installed in a lower part of the light box and connected to an electric control translation platform lead screw, the electric control translation platform lead screw is connected to the stepper motor;
    wherein the line illuminating cylindric box is installed a side above the object to be detected, a photosensitive diode is installed near to the linear light source box and is connected with the linear light source controller, the photosensitive diode senses an intensity variation of the linear light source and inputs feedback signals to the linear source controller;
    wherein the halogen lamp is provided in the linear light source box, the halogen lamp is connected with the linear light source controller;
    wherein the line-scanning camera is installed in an upper part of the light box and right above the object to be detected, the line-scanning camera is connected with the beam splitting system and the computer.

2. The hyperspectral imaging light source system according to claim 1, wherein said linear light source box is a hollow cylinder structure, the axial wall of the hollow cylinder structure is provided with a line slot, and the standard of the wall thickness is opaque and the inner wall is provided with roughness.

* * * * *